United States Patent [19]
Maliszewski et al.

[11] Patent Number: 6,063,371
[45] Date of Patent: May 16, 2000

[54] PHARMACEUTICAL COMPOSITIONS COMPRISING A SOLUBLE INTERLEUKIN-4 RECEPTOR

[75] Inventors: Charles R. Maliszewski, Seattle, Wash.; Fred D. Finkelman, Rockville, Md.

[73] Assignees: Immunex Corporation, Seattle, Wash.; The United States of America as represented by the Secretary of the Army, Washington, D.C.

[21] Appl. No.: 08/714,617

[22] Filed: Sep. 16, 1996

Related U.S. Application Data

[63] Continuation of application No. 08/425,308, Apr. 17, 1995, abandoned, which is a continuation of application No. 08/033,874, Mar. 19, 1993, abandoned.

[51] Int. Cl.$^7$ ............................ A61K 38/17; A61K 38/20
[52] U.S. Cl. .................. 424/85.2; 514/2; 514/8; 514/12; 514/885
[58] Field of Search ................ 530/351; 514/12, 514/2, 8, 885; 424/85.1, 85.2

[56] References Cited

U.S. PATENT DOCUMENTS

| | | | |
|---|---|---|---|
| 4,707,443 | 11/1987 | Nelson et al. | 435/7 |
| 5,057,417 | 10/1991 | Hammonds et al. | 435/69.1 |
| 5,116,951 | 5/1992 | Druez et al. | 530/395 |
| 5,180,678 | 1/1993 | Druez et al. | 436/501 |
| 5,180,812 | 1/1993 | Dower et al. | 530/351 |
| 5,194,375 | 3/1993 | Park et al. | 435/69.1 |
| 5,216,128 | 6/1993 | Novick et al. | 530/350 |

FOREIGN PATENT DOCUMENTS

| | | |
|---|---|---|
| 0 217 577 A2 | 4/1987 | European Pat. Off. |
| 0 367 566 A1 | 5/1990 | European Pat. Off. |
| 0 413 908 | 2/1991 | European Pat. Off. |
| 0 502 599 A1 | 9/1992 | European Pat. Off. |
| 0 538 810 | 4/1993 | European Pat. Off. |
| WO 85/00974 | 3/1985 | WIPO. |
| WO89/09621 | 10/1989 | WIPO. |
| WO90/05522 | 5/1990 | WIPO. |
| WO91/03553 | 3/1991 | WIPO. |
| WO91/09619 | 7/1991 | WIPO. |
| WO91/12022 | 8/1991 | WIPO. |

OTHER PUBLICATIONS

Callard et al. The Cytoleine Facts Book, Academic Press Inc. 1994, p. 64.
Sato et al., "Recombinant Soluble Murine IL–4 Receptor Can Inhibit or Enhance IgE Responses in Vivo," *Journal of Immunology* 150 (7):2717–2723, 1991.
Karavodin, L.M., and L.P. Courtney, *Abstracts of the 8th International Congress of Immunology*, Springer–Verlag, Budapest, p. 220;1992.
Honda et al., *The Journal of Immunology*, 148:2178–2180, No. 7;1992.
Aderka et al., *J. Exp. Med.*, 175:323–329; 1992.
Ashkenazi et al., *Proc. Natl. Acad. Sci. USA*, 88:10535–10539; 1991.
Fernandez–Botran et al., *J. Exp. Med.*, 174:673–684; 1991.
Jacobs et al., *Blood*, 77:2396–2403; 1991.
Lesslauer et al., *Eur. J. Immunol.*, 21:2883–2886; 1991.
Fernandez–Botran et al., *The FASEB Journal*, 5:2567–2574; 1991.
Dower et al., *Jounal of Clinical Immunology*, 10:289–299; 1990.
Maliszewski et al., *The Journal of Immunology*, 144:3028–3033; 1990.
Mosely et al., *Cell*, 59:335–348; 1989.
Urdal, et al., *Behring Inst. Mitt.*, 83:27–29; 1988.
Baumann, et al., *Journal of Clinical Endocrinology and Metabolism*, 64:657–660; 1987.
Rosenblum, et al., *Cancer Research*, 45:2421–2424; 1985.

*Primary Examiner*—Prema Mertz
*Attorney, Agent, or Firm*—Seed and Bery, LLP; Kathryn A. Anderson

[57] ABSTRACT

The biological activity of exogenous ligand proteins is enhanced by intravenously co-administering to a mammal the ligand and a soluble receptor protein that binds thereto. Pharmaceutical compositions comprising a ligand protein complexed with a soluble receptor protein are provided. In certain embodiments, the ligand is selected from the group consisting of interleukins, colony stimulating factors, and tumor necrosis factor.

6 Claims, 3 Drawing Sheets ental compositions comprising a ligand and a soluble receptor that binds the ligand.

PHARMACEUTICAL COMPOSITIONS COMPRISING A SOLUBLE INTERLEUKIN-4 RECEPTOR

CROSS-REFERENCE TO RELATED APPLICATIONS

This application is a continuation of application Ser. No. 08/425,308, filed Apr. 17, 1995, now abandoned, which is a continuation of application Ser. No. 08/033,874, filed Mar. 19, 1993, now abandoned.

BACKGROUND OF THE INVENTION

The term "cytokines" encompasses a diverse group of soluble proteins that are released by one type of cell and mediate a biological effect on another cell type. Biological activities exhibited by cytokines include control of proliferation, growth, and differentiation of various cell types, among which are cells of the hematopoietic or immune systems.

Examples of cytokines include the interleukins (e.g., interleukins 1 through 10), the interferons (IFNα, IFNβ, and IFNγ), tumor necrosis factor (TNFα and TNFβ), and colony stimulating factors. Examples of colony stimulating factors (CSF), which control growth and differentiation of hematopoietic cells, are granulocyte-CSF (G-CSF), granulocyte-macrophage-CSF (GM-CSF), macrophage-CSF (M-CSF or CSF-1), mast cell growth factor (MGF), and erythropoietin (EPO).

The biological activity of cytokines generally is mediated by binding of the cytokine to a receptor specific for that cytokine, located on the surface of target cells. Much research has been directed to identifying receptor(s) that bind a given cytokine (often referred to as the "ligand" for the receptor in question), and exploring the roles that endogenous ligands and receptors play in vivo.

Clinical utility has been demonstrated for a number of cytokines. Methods for enhancing the biological activity of cytokines administered in vivo would be beneficial in order to more fully realize the therapeutic potential of these proteins. Such enhancement of biological activity would allow reduction of the effective therapeutic dosages of cytokines to minimize side effects associated with administration of certain cytokines.

SUMMARY OF THE INVENTION

The present invention provides a pharmaceutical composition comprising a ligand protein and a soluble receptor that binds the ligand. The soluble receptor serves to enhance the biological activity of the exogenous ligand when the pharmaceutical composition is administered to a mammal. The present invention thus provides a method of enhancing the biological activity of an exogenous ligand in vivo by intravenously co-administering to a mammal a ligand and a soluble receptor that binds to the ligand. In certain embodiments of the present invention, the ligand is selected from the group consisting of interleukins, colony stimulating factors, and tumor necrosis factor.

DETAILED DESCRIPTION OF THE INVENTION

Figure 1:
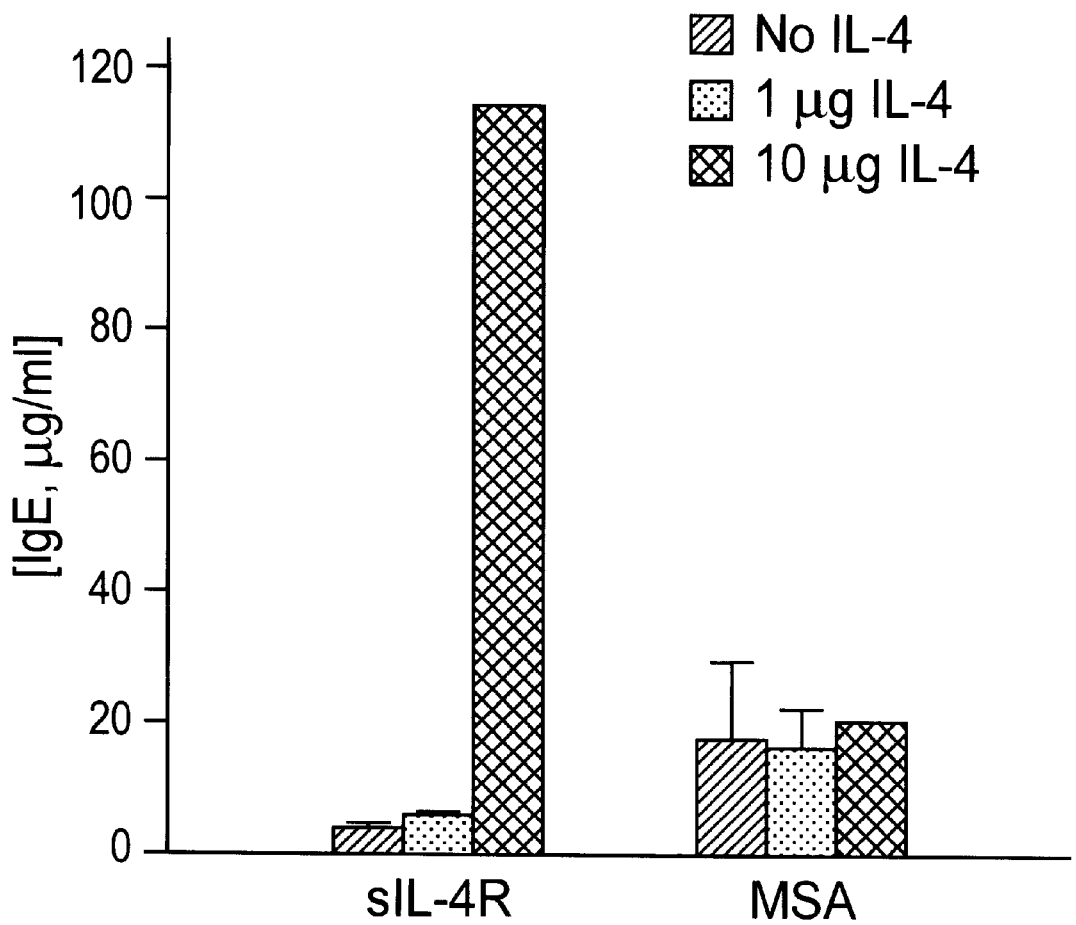
FIG. 1 presents the results of a study of the effect of administering IL-4, pre-mixed with a soluble IL-4 receptor (sIL-4R), on anti-IgD induced IgE secretion in mice. The study is described in Example 1.

The present invention provides a pharmaceutical composition comprising a ligand and a soluble receptor that binds the ligand. The pharmaceutical compositions may further comprise a suitable diluent, excipient, stabilizer, or carrier. The soluble receptor protein serves to increase the biological activity of the exogenous ligand in vivo, compared to the same amount of ligand administered alone. The present invention further provides a method for enhancing a biological activity of an exogenous ligand in vivo by intravenously co-administering to a mammal a ligand and a soluble receptor that binds to the ligand, wherein the biological activity of the administered (exogenous) ligand is increased compared to the biological activity of an equivalent amount of the ligand administered alone (i.e., without the soluble receptor). The inventive method thus offers the advantage of lowering the effective dosage of the exogenous ligand.

By "co-administration" is meant simultaneous administration of the ligand and soluble receptor. The ligand and receptor are combined (e.g., mixed together in a suitable buffered solution) prior to administration to allow formation of the desired ligand-receptor complex. The ligand and receptor may be combined immediately prior to injection or may be incubated in vitro, preferably for no more than 24 hours prior to injection. The pharmaceutical compositions of the present invention generally are administered intravenously.

While not wishing to be bound by theory, the enhanced biological activity achieved in accordance with the present invention may be attributable to the soluble receptor protein's ability to reduce proteolytic degradation or increase the serum half life of the ligand complexed therewith. A complex forms via the binding of the ligand to the soluble receptor. The complex is believed to dissociate in vivo, releasing the ligand in the manner of a slow release formulation. In the complexes employed in the present invention, the ligand desirably is non-covalently and reversibly bound to the soluble receptor, as opposed to being covalently cross-linked using chemical cross-linking reagents, for example.

The binding affinity of the receptor for the ligand desirably is low enough so that the ligand is released therefrom in vivo, preferably in the manner of a slow release formulation. The ligand released from the complex is free to bind to endogenous receptors on target cells in vivo to effect a desired biological response. The binding affinity desirably is high enough so that the benefits of complex formation disclosed herein are realized. Binding affinities of a number of receptors for their respective ligands are known (see for example Urdal and Park, *Behring Inst. Mitt.*, no. 83, pp 27–39, 1988, at page 29, and Dower et al., *J. Clin. Immunol.*, 10:289, 1990 at page 294) and can be determined for other receptors using conventional techniques.

The relative concentrations of soluble receptor to ligand are to be considered in preparing the pharmaceutical compositions of the present invention. As described in examples 1–3 with respect to the IL-4 embodiment of the invention, the ability of the soluble receptor to enhance rather than inhibit ligand activity in vivo was dependent on the relative concentrations of the two proteins. Receptor and ligand were administered to mice in different ratios to determine the preferred relative concentrations. Preferred ratios can be determined for other receptor-ligand combinations using routine assay procedures.

The mammal to which the pharmaceutical compositions of the present invention are administered is any mammal for which enhancement of the biological activity of an exogenous ligand is desired. Mammalian species to which the inventive compositions may be administered include, but are not limited to, human, simian, bovine, porcine, equine, and murine species. The ligand and receptor proteins employed in the pharmaceutical compositions desirably are derived from from same species as the mammal to which they are to be administered.

The pharmaceutical compositions may be administered for purposes that include therapy or research studies, for example. The compositions contain the ligand and receptor proteins in amounts effective for the intended use. Therapeutically effective dosages will, of course, vary according to such factors as the particular ligand and receptor employed, the nature of the disorder to be treated, and the size and condition of the patient The receptor or ligand proteins, or both, may be labeled with a detectable reagent (e.g., radiolabeled) for such purposes as monitoring biodistribution of the proteins in vivo.

The ligand protein is any ligand having a biological activity that is to be enhanced in vivo and which will bind to a corresponding receptor protein. Among the useful ligands are cytokines, defined above. In certain embodiments of the present invention, the ligand is a protein selected from the group consisting of the interleukins (e.g., interleukins 1 through 10), the interferons (IFN$\alpha$, IFN$\beta$, and IFN$\gamma$), tumor necrosis factor (TNF$\alpha$ and TNF$\beta$), and colony stimulating factors. Examples of colony stimulating factors (CSF), which control growth and differentiation of hematopoietic cells, are granulocyte-CSF (G-CSF), granulocyte-macrophage-CSF (GM-CSF), macrophage-CSF (M-CSF or CSF-1), mast cell growth factor (MGF), and erythropoietin (EPO).

Any soluble receptor protein that binds a particular ligand may be employed. The term "receptor" is used in accordance with the term's conventional meaning in the context of receptor-ligand binding, and is not to be construed as encompassing antibodies. The term "soluble" distinguishes the receptors used in the present invention from their cell membrane-bound counterparts, as is understood in the field of cytokine receptors. Soluble receptors comprise an extracellular (ligand binding) domain, but lack the transmembrane region that causes retention of a receptor on the cell surface. The soluble receptors generally lack the intracellular (cytoplasmic) domain as well.

Naturally occurring soluble forms of certain receptors are known to exist. Alternatively, DNA encoding a soluble form of a receptor may be derived from DNA encoding the corresponding membrane-bound form using conventional recombinant DNA techniques. A DNA fragment is derived from the extracellular domain of the receptor and the soluble receptor encoded by the DNA fragment is expressed using a suitable host cell/expression vector system. Monomeric, dimeric, or higher multimeric forms of soluble receptors may be employed.

In one embodiment of the present invention, the ligand is interleukin-4 (IL-4), also known as B-cell stimulating factor or BSF-1. Co-administration of a soluble IL-4 receptor (sIL-4R) and IL-4 results in enhancement of the exogenous IL-4 protein's biological activity in vivo, compared to the biological activity of an equivalent amount of IL-4 administered alone. This phenomenon is dependent on the relative concentrations of IL-4 and sIL-4R. The molar ratio of sIL-4R to IL-4 administered in accordance with the present invention generally is from 30:1 to 1:1; preferably from 5:1 to 1:1; most preferably 1:1.

As described in examples 1–3, co-administration of a soluble IL-4R protein with IL-4 resulted in superinduction of an IL-4-mediated IgE response in mice. While sIL-4R can block IgE secretion by binding endogenous IL-4, sIL-4R also can enhance the IgE secretion-inducing activity of exogenous IL-4. These positive and negative effects of sIL-4R on IL-4 are dependent upon the relative concentrations of the two proteins. Additionally, the soluble IL-4 receptor protein was not found to enhance the ability of endogenous IL-4 (the IL-4 naturally present within the mammal) to stimulate IgE production.

Biological activities mediated by IL-4 include those described by Mosley et al. (*Cell*, 59:335, 1989, at page 335). The activities include, but are not limited to, stimulating the proliferation of activated B cells, inducing expression of class II major histocompatibility complex determinants on resting B cells, enhancing expression and secretion of IgE and IgG1 isotypes by resting B cells, and enhancing expression of CD23 on the surface of B cells.

Pharmaceutical compositions of the present invention comprising IL-4 and sIL-4R may be administered to tumor-bearing mammals to enhance anti-tumor immunity. IL-4 induces anti-tumor immunity via induction of cytotoxic T-lymphocytes. In view of IL-4's ability to inhibit macrophages, the inventive compositions may be used to treat inflammatory diseases such as arthritis. These compositions comprising IL-4-sIL-4R complexes also may be administered to treat autoimmune diseases, e.g., multiple sclerosis or rheumatoid arthritis, or to inhibit graft versus host disease following transplantation of organs or tissue.

Methods for producing and purifying IL-4 are known. See, for example, EP 254,399, which discloses the nucleotide sequence of an isolated cDNA encoding murine IL-4 and describes procedures for purifying naturally occurring and recombinant murine IL-4. A recombinant vector comprising DNA encoding a murine IL-4 protein was deposited in *E. coli* RR1 host cells with the American Type Culture Collection on Apr. 25, 1986, and assigned accession no. ATCC 67104. Production and purification of recombinant murine IL-4 are also described by Grabstein et al. (*J. Exp. Med.* 163:1405, 1986). Production and purification of recombinant human IL-4 has been described by Solari et al. (*Biochem. J.*, 262:897, 1989).

Soluble interleukin-4 receptor proteins (sIL-4R) are known, along with methods for producing and purifying such proteins. Naturally occurring soluble murine IL-4R has been described in EP 367,566 and by Mosley et al. *Cell*, 59:335, 1989. EP 367,566 also describes the cloning of murine and human IL-4R cDNA and preparation of soluble human IL-4R.

Receptors for other interleukins have been described, among which are two distinct interleukin-1 receptors designated type I and type II, described in U.S. Pat. No. 4,968,607 (type I IL-1R), U.S. Pat. No. 5,180,812 (directed specifically to soluble type I IL-1R), and PCT application no. WO 91/18982 (type II IL-1R). The two IL-1 receptor proteins each bind both IL-1$\alpha$ and IL-1$\beta$. An interleukin-2 receptor has been described in U.S. Pat. No. 4,578,335 and EP 162,699. The IL-2 receptor has been found to comprise two subunits designated α and β, each of which can bind IL-2, as described by Hatakeyama et al. (*Science* 244:42, 1989). Itoh et al. (*Science,* 247:324, 1990) report the cloning of an interleukin-3 receptor gene. A receptor for interleukin-6 has been described by Yamasaki et al. (*Science* 241:825, 1988), and Taga et al. (*Cell* 58:573–581) describe production of a recombinant soluble IL-6R. An interleukin-7 receptor is disclosed in U.S. Pat. No. 5,194,375.

In another embodiment of the present invention, the ligand is tumor necrosis factor (TNF). Pharmaceutical compositions comprising complexes of sTNF-R and TNF, as described herein, may be used as immune system stimulants and may be administered as a therapeutic agent to tumor-bearing mammals.

TNFα, also known as cachectin, and TNFβ, also known as lymphotoxin, are homologous mammalian secretory proteins capable of inducing a number of effects on a variety of cell types. The great similarity in the stuctural and functional characteristics of these two cytokines has resulted in their collective description as TNF. Isolation of cDNA encoding TNFα has been reported by Pennica et al. (*Nature* 312:724, 1984) and the cloning of TNFβ cDNA has been described by Gray et al. (*Nature* 312:721, 1984). Recombinant human TNFβ is available from R&D Systems, Minneapolis, Minn.

Two distinct TNF receptor proteins have been identified, namely, type I TNF-R (also known as p60 TNF-R or TNF-Rα) and type II TNF-R (also known as p80 TNF-R or TNF-Rβ). Both of these receptors, which bind both TNFα and TNFβ, are described in EP 422,339. The p80 TNF-R also is described in EP 418,014. As described on page 14 of EP 418,014, a recombinant expression vector comprising human p80 TNF-R cDNA was deposited with the American Type Culture Collection on Sep. 6, 1989, and assigned accession no. ATCC 68088. Production of soluble forms of both TNF receptors is also described in Lesslauer et al. (*Eur. J. Immunol.,* 21:2883, 1991). The ratio of sTNF-R to TNF administered in accordance with the present invention preferably is 1:1, most preferably less than 1:1, by weight.

Monomeric and dimeric forms of TNF-R have been produced and demonstrated to bind TNF, with the dimer exhibiting higher affinity for the ligand. One such dimer comprises two fusion proteins, each comprising the extracellular domain of p80 TNF-R fused to the N-terminus of an Fc domain polypeptide isolated from a human IgG1 antibody. Disulfide bonds form between the Fc moieties of two such fusion proteins, producing the dimer. Production of such dimers has been described by Ashkenazi et al. (*Proc. Natl. Acad. Sci. USA* 8810535, 1991), for example.

In another embodiment of the present invention, the ligand is a colony stimulating factor (CSF). Examples of colony stimulating factors are granulocyte-CSF (G-CSF), granulocyte-macrophage-CSF (GM-CSF), macrophage-CSF (M-CSF or CSF-1), mast cell growth factor (MGF), and erythropoietin (EPO).

In particular embodiments of the present invention, the ligand is GM-CSF or G-CSF. The biological activities of GM-CSF include those described by Gough and Nicola in *Colony Stimulating Factors: Molecular and Cellular Biology,* Dexter et al., eds., Marcel Dekker, New York, 1989, pp 111–153. GM-CSF has therapeutic uses that include but are not limited to increasing the numbers of granulocytes and macrophages, e.g., in patients who have undergone bone marrow transplantation. G-CSF may be administered to increase the granulocyte count in patients who have undergone chemotherapy.

A number of receptors for CSFs have been identified, among which is the EPO receptor disclosed by D'Andrea et al. (*Cell,* 57:277, 1989). The cloning of cDNA encoding a receptor for human GM-CSF has been described by Gearing et al. (*Embo J.,* 8:3667, 1989). Fukunaga et al. (*Cell,* 61:341, 1990) report the cloning of cDNA encoding a murine G-CSF receptor.

Ligand and receptor proteins that differ in amino acid sequence from the native forms of the proteins, but which still possess the desired biological activity, may be employed in the present invention. For ligands, the variant protein will possess a biological activity of the native protein that is to be enhanced by co-administration with the receptor in accordance with the present invention. For receptors, the desired biological activity is the ability to bind to the ligand.

Examples of such variant proteins include, but are not limited to those comprising conservative amino acid substitutions or modification of the amino acid sequence to inactivate N-glycosylation or KEX2 protease processing sites. Other variants include recombinant proteins truncated at the N- or C-terminus as a result of differential processing, e.g., in various host cell types, or comprising terminal or internal truncations produced using conventional recombinant DNA techniques.

In one embodiment, the ligand or receptor protein is encoded by a DNA that differs in nucleotide sequence from the native DNA sequence, but that hybridizes to the native DNA under moderately stringent conditions. The hybridizing non-native DNA encodes a ligand or receptor protein that possesses the desired biological activity. The skilled artisan will recognize that, due to the degeneracy of the genetic code, a DNA sequence may vary from a native DNA sequence that encodes a particular protein, but still encode an amino acid sequence identical to that of the native protein.

The pharmaceutical compositions of the present invention may comprise suitable carriers, diluents, excipients, stabilizers, or other such components as are conventionally used in pharmaceutical formulations. Physiologically acceptable carriers, diluents, excipients, or stabilizers may be included at concentrations that will be nontoxic to recipients at the intended dosages. The inventive compositions may comprise buffers; antioxidants such as ascorbic acid; carbohydrates including glucose, sucrose, or dextrans; chelating agents such as EDTA; glutathione, or other stabilizers and excipients. Neutral buffered saline is an example of an appropriate diluent.

The following examples are provided to illustrate certain embodiments of the present invention, and are not to be construed as limiting the scope thereof.

EXAMPLE 1

Co-administration of IL-4 and a Soluble IL-4 Receptor

Injection of mice with foreign polyclonal or monoclonal antibodies directed against mouse IgD stimulates polyclonal B cell activation and secretion of large amounts of IgE and IgG1 (Finkelman et al., *J. Immunol.* 129:638, 1982; Finkelman et al., *J. Immunol.* 138:2826, 1987). The increase in serum IgE is dependent upon the action of IL-4, as treatment of mice with an anti-IL-4 antibody at the time of anti-IgD administration completely ablates the IgE response but has no effect upon IgG1 secretion (Finkelman et al., *Proc. Natl. Acad. Sci. USA* 83:9675, 1986; Finkelman et al., *J. Immunol.* 141:2335, 1988; Finkelman et al., *J. Immunol.* 142:403, 1989). This IL-4 dependent IgE response model was employed in the present study to assess the effect of exogenous sIL-4R on the in vivo biological activity of exogenous IL-4.

Murine sIL-4R

Recombinant murine sIL-4R was produced in HeLa cells transfected with a murine sIL-4R cDNA subcloned into a mammalian expression vector. A transfectant clone designated HeLa E363, described in Jacobs et al. (*Blood* 77:2396, 1991), secreted high levels of sIL-4R and was chosen for use in the study. Culture supernatant was diluted in 25 mM β-alanine and incubated at pH 4 to precipitate contaminant proteins. The supernatant was then diluted in 100 mM Tris/1.5 M ammonium sulfate, pH 8, and loaded onto a hydrophobic interaction chromatography (HIC) Phenyl-Sepharose fast flow column. The product was eluted using a decreasing ammonium sulfate concentration gradient and the fractions containing murine sIL-4R were pooled. Pooled material was loaded onto a ConA-Sepharose column and the product was eluted with 100 mM Tris/300 mM methyl-mannopyranoside, pH 8. At this point, the product was >90% pure as determined by SDS-PAGE and reverse phase HPLC. Purified material had an average molecular weight of ~39,000 as determined by SDS-PAGE.

Human sIL-4R

Human sIL-4R may be prepared as follows for use in a pharmaceutical composition of the present invention. A mammalian expression vector encoding a soluble version of the human IL-4R was constructed by ligating cDNA encoding only the extracellular region of the full length human IL-4R (Idzerda et al., *J. Exp. Med.* 171:861, 1990) into a mammalian expression vector. Human sIL-4R was purified by a two step process from culture supernatant of CHO cells transfected with the sIL-4R vector. Harvested supernatant was diluted fourfold, adjusted to pH 8, and loaded onto a Q-Sepharose fast flow anionic exchange column. The column was washed with 25 mM Tris, pH 8, and the product was step eluted with 25 mM Tris/150 mM NaCl, pH 8. The Q-Sepharose pool was diluted fivefold with deionized water and incubated in 40% acetonitrile overnight to inactivate an acid protease that degraded the product a pH <6. The product was then diluted in 50 mM citrate, pH 3, and loaded onto a carboxy sulfon cation exchange column. Soluble IL-4R was step eluted from this column with 75 mM acetate, pH 9. The product was greater than 95% pure by SDS-PAGE and C-18 reverse phase HPLC. Purified material had an average molecular weight of ~39,000 as determined by SDS-PAGE.

IL-4

Murine rIL-4 was produced in yeast and purified to homogeneity as previously described (Grabstein et al., *J. Exp. Med.* 163:1405, 1986).

Generation of in vivo IgE responses

In vivo experiments were performed with 8 to 12 week-old female BALB/c mice (The Jackson Laboratory, Bar Harbor, Me.). Anaesthetized BALB/c mice (3 animals/group) were immunized by retroorbital i.v. injection with 100 μg each of H8$^{a/t}$ and FF1-4D5 allo-anti-mouse IgD mAbs in pyrogen-free saline. Murine IL-4 and murine sIL-4R were injected intraperitoneally twice daily on days 3, 4, and 5. These timepoints were chosen in view of the results of a previous study demonstrating that IL-4 secretion first increases 3 days after anti-IgD treatment (Finkelman et al., *J. Immunol.* 137:2878, 1986). Combinations of IL-4 and sIL-4R were mixed in a saline solution and incubated overnight at 4° C. prior to injection. Blood was collected from treated mice nine days after anti-IgD treatment, clotted overnight at 4° C., and serum was collected after centrifugation and stored at −20° C. until assayed.

Serum IgE and IgG1 assays

Immunoglobulin levels were determined by an isotype specific sandwich ELISA technique as previously described (Maliszewski et al., *J. Immunol.* 144:3028, 1990). For the IgG1 assay, unconjugated and horseradish peroxidase-conjugated affinity purified goat anti-mouse isotype specific reagents (Southern Biotechnology Associates, Inc., Birmingham, AB) were used as capture and second step reagents, respectively. Reference curves for IgG1 quantification were generated with isotype matched murine myeloma proteins (Southern) as standards. For the IgE assay, a rat anti-mouse IgE mAb was used as capture step reagent; biotinylated rat anti-mouse IgE (Bioproducts for Science, Inc., Indianapolis, Ind.) was used as second step reagent; and horseradish peroxidase-conjugated streptavidin (Zymed) was used in the third step. Reference curves for IgE quantification were established with a murine anti-dinitrophenol specific IgE myeloma antibody, A3B4, provided by Dr. Tom Waldschmidt, University of Iowa.

Effects of exogenous IL-4 upon IgE inhibition by sIL-4R

The effect of exogenous IL-4, administered with or without sIL-4R, on anti-IgD induced IgE secretion in mice was determined in the following manner. Mice (3 animals per group) were immunized on day 0 with anti-IgD and injected intraperitoneally twice daily on days 3, 4, and 5 with IL-4 (1 or 10 μg/day) that had been premixed with murine sIL-4R or murine serum albumin (MSA) (each at 300 μg/day). Mice were bled on day 9 and serum IgE levels were determined by ELISA. Results are presented in FIG. 1 as mean concentration +/− the standard error of the mean (SEM).

As shown in FIG. 1, the administration of IL-4 (1 or 10 μg/day) by itself had little or no effect upon serum IgE concentration in anti-IgD treated mice. The sIL-4R (300 μg/day) was inhibitory when administered by itself and its activity was partially reversed by the coadministration of the lower dose of IL-4 (1 μg/day). In marked contrast, co-administering the sIL-4R and the higher (10 μg/day) dose of IL-4 not only reversed the inhibitory effect of sIL-4R, but also enhanced IgE production to levels over fivefold greater than those in anti-IgD treated mice that had been injected with IL-4 alone. Thus, concomitant administration of exogenous IL-4 and IL-4R had a superinductive effect upon IgE secretion by anti-IgD treated mice.

EXAMPLE 2

Co-administration of sIL-4R and IL-4: IL-4 Dose Response Study

An additional study was conducted in which IL-4 was administered at several different concentrations together with 300 μg of sIL-4R. This dosage of sIL-4R had been found to inhibit anti-IgD-induced IgE secretion in the absence of exogenous IL-4 (see example 1). Anti-IgD treated mice (3 animals/group) were injected intraperitoneally twice daily on days 3, 4, and 5 with murine sIL-4R (300 μg/day) or murine serum albumin (MSA) (300 μg/day) that had been premixed with various concentrations of IL-4 (0, 1, 2, 5, or 10 μg/day). The materials and experimental procedures were as described in example 1. The results are presented in FIG. 2 as mean concentration of IgE +/−SEM.

Figure 2:
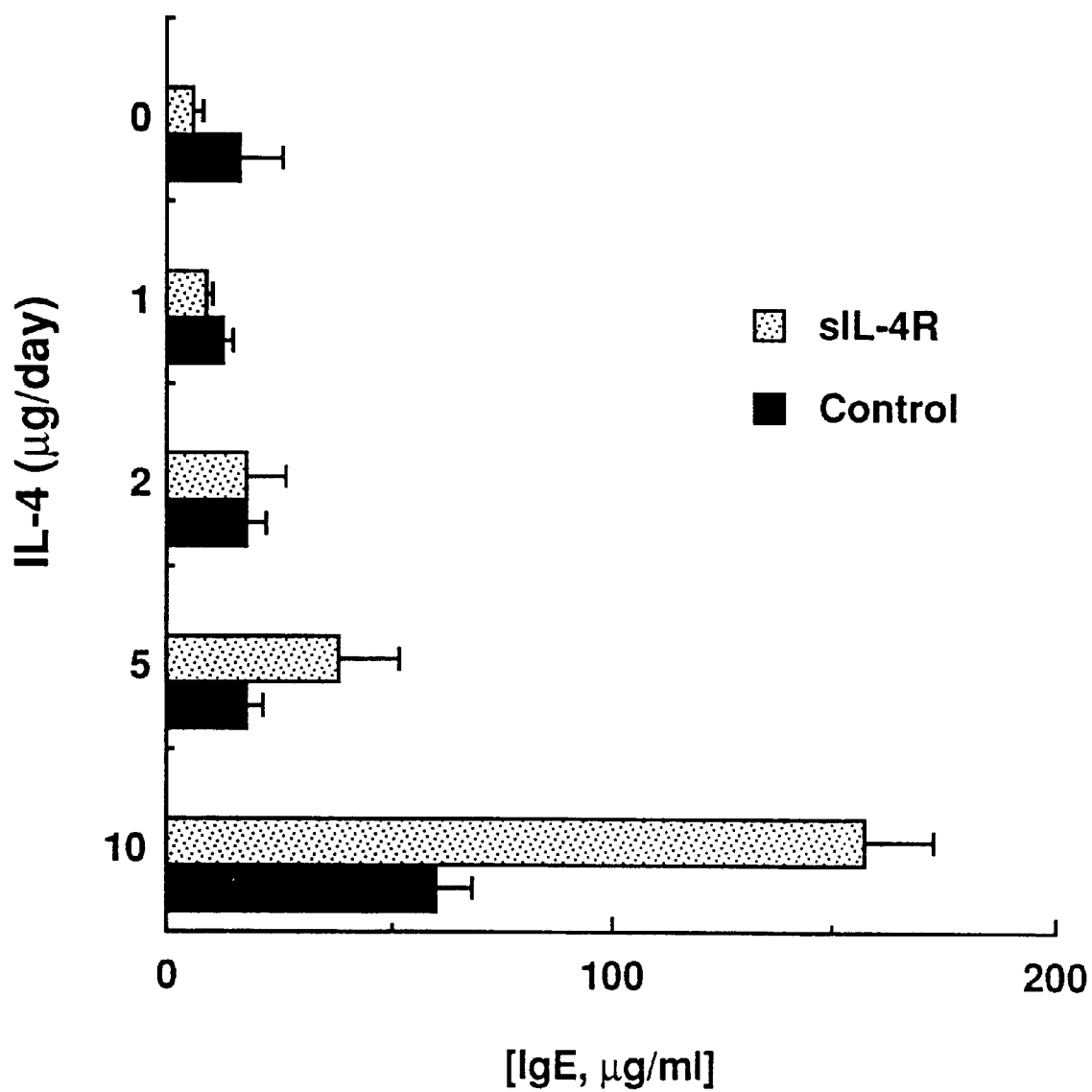
FIG. 2 presents the results of the IL-4 dose response study described in Example 2. Various concentrations of IL-4 pre-mixed with a constant amount of sIL-4R were administered to mice, and levels of anti-IgD induced IgE secretion in the mice were measured.

The data in FIG. 2 demonstrate that in the presence of exogenous IL-4, the inhibitory effects of sIL-4R were reversed to superinductive effects in a dose dependent manner. Coadministration of 300 μg/day sIL-4R and 5–10 μg/day IL-4 resulted in a 2–3 fold increase in IgE secretion compared with mice treated with anti-IgD plus IL-4 alone.

EXAMPLE 3

Co-administration of sIL-4R and IL-4: sIL-4R Dose Response Study

Figure 3:
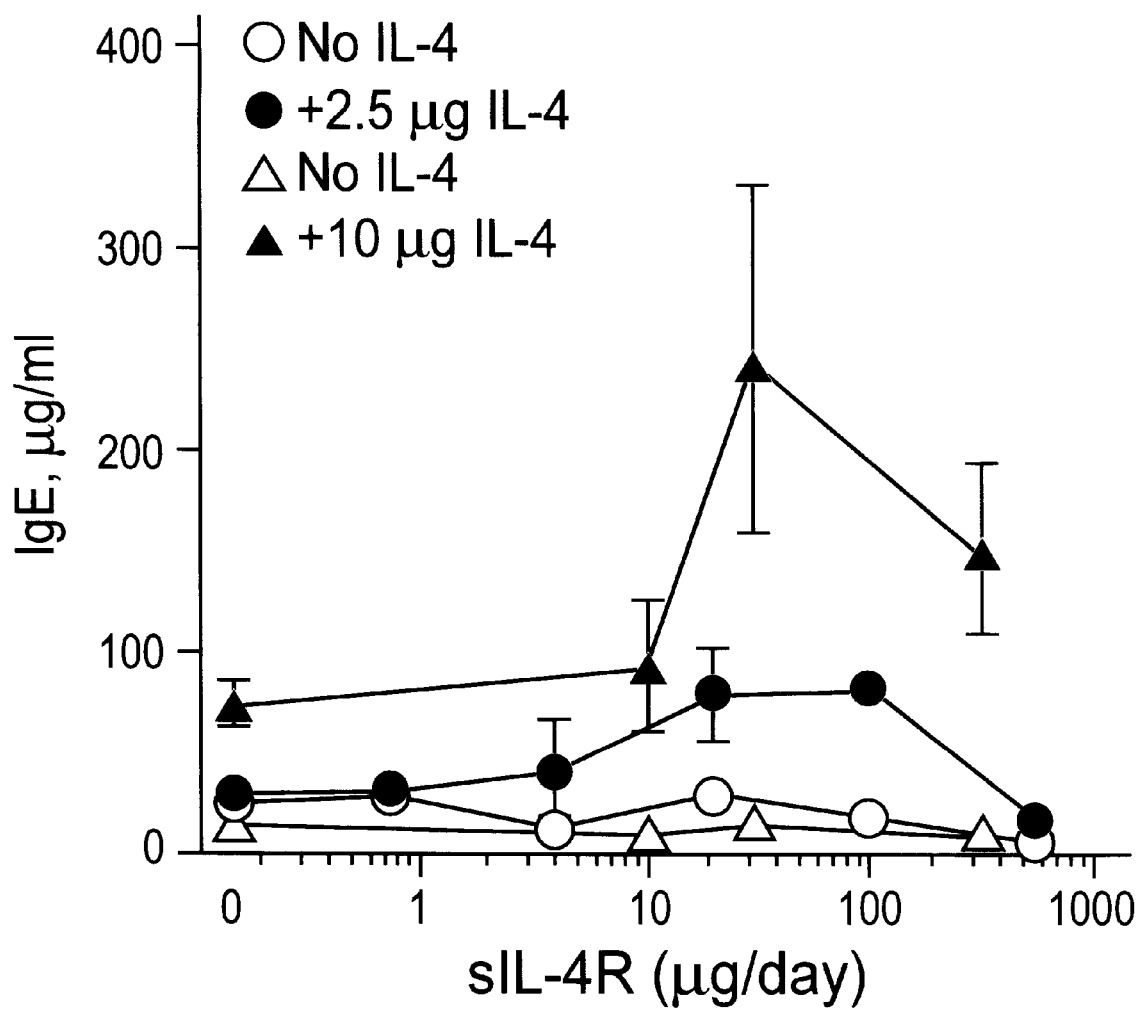
FIG. 3 presents the results of the sIL-4-R dose response study described in Example 3. Various concentrations of sIL-4R pre-mixed with a constant amount of IL-4 were administered to mice, and levels of anti-IgD induced IgE secretion in the mice were measured.

The superinductive effect was further examined in two separate sets of experiments by varying the dose of sIL-4R used for coinjection with a constant dose of IL-4. The results of the study, conducted as follows using the materials and experimental procedures described in example 1, are presented in FIG. 3. Anti-IgD treated mice (3 animals per group) were injected intraperitoneally twice daily on days 3, 4, and 5 with various concentrations of murine sIL-4R (0, 1, 10, 100, or 1000 μg/day) with (closed symbols) or without (open symbols) IL-4. The results are from two separate sets of experiments, the first using 2.5 μg/day of exogenous IL-4 (circles) and the second using 10 μg/day of exogenous IL-4 (triangles). Results are presented as mean concentration of IgE +/−SEM.

In the first experiment, sIL-4R at 20–100 μg/day plus IL-4 (2.5 μg/day) caused an approximately 3-fold increase in IgE secretion compared with mice treated with 2.5 μg of IL-4 alone. However, a higher dose of sIL-4R (1000 μg/day) resulted in an inhibited IgE response, even in the presence of exogenous IL-4. The second experiment using a higher dose of exogenous IL-4 (10 μg/day) yielded a similar pattern of activities. Thus, the in vivo biological activity of exogenous IL-4 on IgE production is significantly enhanced by sIL-4R. This effect is highly concentration dependent, in that the stimulatory effects of exogenous IL-4 were reversed when 1000 μg/day of sIL-4R was co-administered with 2.5 μg or 10 μg IL-4 (i.e., when the molar ratio of sIL-4R:IL-4 was 200:1 or 50:1).

In the same study, IL-4 administered in the presence or absence of sIL-4R failed to enhance IgG1 production (data not shown). This result was as expected, since IgG1 production is not believed to be mediated by IL-4.

What is claimed is:

1. A method of enhancing a biological activity of interleukin-4 (IL-4) in vivo, comprising intravenously co-administering to a mammal IL-4 and a soluble IL-4 receptor (sIL-4R), wherein the mammal is afflicted with a condition for which enhancement of the biological activity of the IL-4 is desired, and wherein the sIL-4R and IL-4 are co-administered in a molar ratio ranging from 30:1 to 1:1.

2. A method according to claim 1, wherein the sIL-4R and IL-4 are co-administered in a molar ratio ranging from 5:1 to 1:1.

3. The method according to any one of claims 1, or 2 wherein said sIL-4R and IL-4 are human sIL-4R and human IL-4.

4. A pharmaceutical composition comprising interleukin-4 (IL-4) and a soluble IL-4 receptor (sIL-4R), wherein the composition comprises sIL-4R and IL-4 in a molar ratio ranging from 30:1 to 1:1.

5. A pharmaceutical composition according to claim 4, wherein the composition comprises sIL-4R and IL-4 in a molar ratio ranging from 5:1 to 1:1.

6. The pharmaceutical composition according to any one of claim 4 or 5 wherein said sIL-4R and IL-4 are human sIL-4R and human IL-4.

* * * * *